(12) United States Patent
Davis et al.

(10) Patent No.: US 9,198,610 B2
(45) Date of Patent: *Dec. 1, 2015

(54) BLOOD SAMPLING DEVICE

(71) Applicant: Becton, Dickinson and Company, Franklin Lakes, NJ (US)

(72) Inventors: Bryan G. Davis, Sandy, UT (US); Jonathan Karl Burkholz, Salt Lake City, UT (US); Minh Quang Hoang, Sandy, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 33 days.

This patent is subject to a terminal disclaimer.

(21) Appl. No.: 13/753,244

(22) Filed: Jan. 29, 2013

(65) Prior Publication Data

US 2013/0121897 A1    May 16, 2013

Related U.S. Application Data

(62) Division of application No. 12/831,891, filed on Jul. 7, 2010, now Pat. No. 8,383,044.

(60) Provisional application No. 61/224,208, filed on Jul. 9, 2009.

(51) Int. Cl.
*A61B 5/15* (2006.01)
*A61B 5/157* (2006.01)
*A61B 5/155* (2006.01)

(52) U.S. Cl.
CPC ............... *A61B 5/157* (2013.01); *A61B 5/1405* (2013.01); *A61B 5/155* (2013.01); *A61B 5/150992* (2013.01)

(58) Field of Classification Search
CPC ..... A61B 5/15; A61B 5/150992; A61B 5/157
See application file for complete search history.

(56) References Cited

U.S. PATENT DOCUMENTS

| 3,859,998 A | 1/1975 | Thomas et al. |
|---|---|---|
| 4,003,403 A | 1/1977 | Nehring |

(Continued)

FOREIGN PATENT DOCUMENTS

| EP | 0 396 016 A2 | 11/1990 |
|---|---|---|
| JP | H11-235330 | 8/1999 |

(Continued)

OTHER PUBLICATIONS

Elson Silva, PhD, "Respecting Hydrology Science in the Patenting System," pp. 1-7, Jan. 13, 2011.

*Primary Examiner* — Paul Hyun
(74) *Attorney, Agent, or Firm* — Jeanne Lukasavage; Craig Metcalf; Kirton McConkie

(57) ABSTRACT

A blood sampling device useful for collecting a blood sample from a separate vascular access device is described herein. The blood sampling device includes a body shaped and sized for partial insertion into a separate vascular access device. The body includes a reservoir defined within the body, which has an internal volume sufficient to contain enough blood for use in a diagnostic blood test. The body also includes a gas permeable vent disposed on the body, in which the gas permeable vent is in gaseous communication with the reservoir. When connected to a separate vascular access device the blood sampling device collects a blood sample as blood flows into the reservoir from the separate vascular access device and as gases pass out the reservoir via the gas permeable vent.

18 Claims, 12 Drawing Sheets

(56) References Cited

U.S. PATENT DOCUMENTS

| | | | |
|---|---|---|---|
| 4,193,399 | A | 3/1980 | Robinson |
| 4,193,400 | A | 3/1980 | Loveless et al. |
| 4,269,186 | A | 5/1981 | Loveless et al. |
| 4,365,630 | A | 12/1982 | McFarlane |
| 4,444,203 | A | 4/1984 | Engelman |
| 4,464,177 | A * | 8/1984 | McGaughey et al. .... 604/168.01 |
| 4,595,021 | A | 6/1986 | Shimizu et al. |
| 4,682,980 | A | 7/1987 | Suzuki |
| 4,765,588 | A | 8/1988 | Atkinson |
| 4,894,052 | A | 1/1990 | Crawford |
| 4,904,240 | A | 2/1990 | Hoover |
| 4,917,671 | A | 4/1990 | Chang |
| 4,935,010 | A | 6/1990 | Cox et al. |
| 4,966,586 | A | 10/1990 | Vaillancourt |
| 5,032,116 | A | 7/1991 | Peterson et al. |
| 5,049,130 | A | 9/1991 | Powell |
| 5,066,284 | A | 11/1991 | Mersch et al. |
| 5,226,883 | A | 7/1993 | Katsaros et al. |
| 5,242,411 | A | 9/1993 | Yamamoto et al. |
| 5,251,873 | A | 10/1993 | Atkinson et al. |
| 5,295,657 | A | 3/1994 | Atkinson |
| 5,295,658 | A | 3/1994 | Atkinson et al. |
| 5,295,969 | A | 3/1994 | Fischell et al. |
| 5,295,970 | A | 3/1994 | Clinton et al. |
| 5,338,313 | A | 8/1994 | Mollenauer et al. |
| 5,342,316 | A | 8/1994 | Wallace |
| 5,417,664 | A | 5/1995 | Felix et al. |
| 5,441,487 | A | 8/1995 | Vedder |
| 5,474,544 | A | 12/1995 | Lynn |
| 5,501,426 | A | 3/1996 | Atkinson et al. |
| 5,501,671 | A | 3/1996 | Rosen et al. |
| 5,533,708 | A | 7/1996 | Atkinson et al. |
| 5,542,932 | A | 8/1996 | Daugherty |
| 5,549,651 | A | 8/1996 | Lynn |
| 5,697,914 | A | 12/1997 | Brimhall |
| 5,702,383 | A | 12/1997 | Giesler et al. |
| 5,749,857 | A | 5/1998 | Cuppy |
| 5,820,596 | A | 10/1998 | Rosen et al. |
| 5,824,001 | A | 10/1998 | Erskine |
| 5,919,160 | A | 7/1999 | Sanfilippo, II |
| 5,954,657 | A | 9/1999 | Rados |
| 5,957,898 | A | 9/1999 | Jepson et al. |
| 5,980,492 | A | 11/1999 | Rosen et al. |
| 5,984,895 | A | 11/1999 | Padilla et al. |
| 6,139,534 | A | 10/2000 | Niedospial, Jr. et al. |
| 6,171,287 | B1 | 1/2001 | Lynn et al. |
| 6,261,282 | B1 | 7/2001 | Jepson et al. |
| 6,344,033 | B1 | 2/2002 | Jepson et al. |
| 6,503,225 | B1 | 1/2003 | Kirsch et al. |
| 6,533,760 | B2 | 3/2003 | Leong |
| 6,533,770 | B1 | 3/2003 | Lepulu et al. |
| 6,595,964 | B2 | 7/2003 | Finley et al. |
| 6,638,252 | B2 | 10/2003 | Moulton et al. |
| 6,651,956 | B2 | 11/2003 | Miller |
| 6,669,681 | B2 | 12/2003 | Jepson et al. |
| 6,786,891 | B2 | 9/2004 | Hiejima |
| 6,866,656 | B2 | 3/2005 | Tingey et al. |
| 6,908,459 | B2 | 6/2005 | Harding et al. |
| 8,383,044 | B2 | 2/2013 | Davis et al. |
| 2001/0047187 | A1 | 11/2001 | Milo et al. |
| 2002/0193752 | A1 | 12/2002 | Lynn |
| 2003/0040760 | A1 | 2/2003 | Hnojewyj et al. |
| 2003/0072676 | A1 | 4/2003 | Fletcher-Haynes et al. |
| 2004/0116830 | A1 | 6/2004 | Trudeau et al. |
| 2005/0015071 | A1 | 1/2005 | Brimhall |
| 2005/0027256 | A1 | 2/2005 | Barker et al. |
| 2005/0077225 | A1 | 4/2005 | Usher et al. |
| 2005/0256457 | A1 | 11/2005 | Rome |
| 2005/0256500 | A1 | 11/2005 | Fujii |
| 2005/0273019 | A1 | 12/2005 | Conway et al. |
| 2005/0283093 | A1 * | 12/2005 | Conway et al. ............... 600/576 |
| 2006/0009713 | A1 | 1/2006 | Flaherty |
| 2008/0200903 | A1 | 8/2008 | Christensen et al. |
| 2008/0200904 | A1 | 8/2008 | Cluff et al. |
| 2008/0255473 | A1 | 10/2008 | Dalebout et al. |
| 2008/0287906 | A1 | 11/2008 | Burkholz et al. |
| 2009/0099431 | A1 | 4/2009 | Dalebout et al. |
| 2009/0312722 | A1 | 12/2009 | Laurent et al. |
| 2010/0042048 | A1 | 2/2010 | Christensen |
| 2010/0057004 | A1 | 3/2010 | Christensen et al. |

FOREIGN PATENT DOCUMENTS

| | | |
|---|---|---|
| JP | 2001-224575 | 8/2001 |
| WO | 2005/104947 A1 | 11/2005 |
| WO | 2006/088501 A1 | 8/2006 |

* cited by examiner

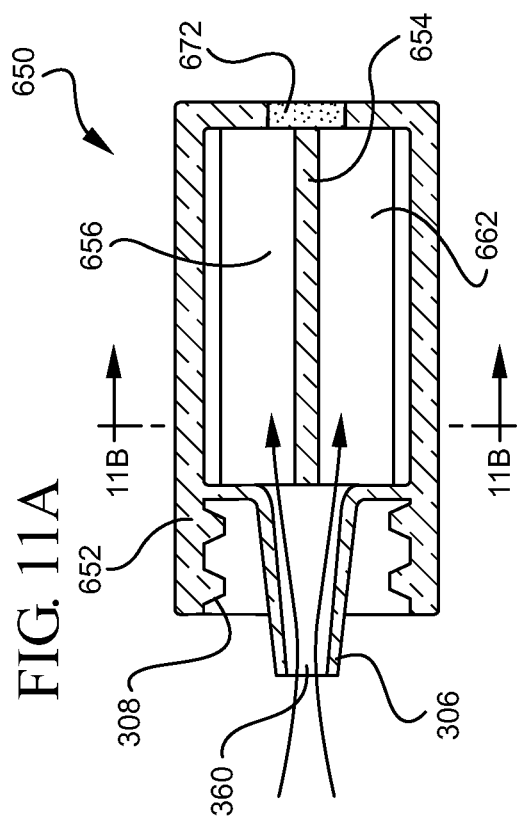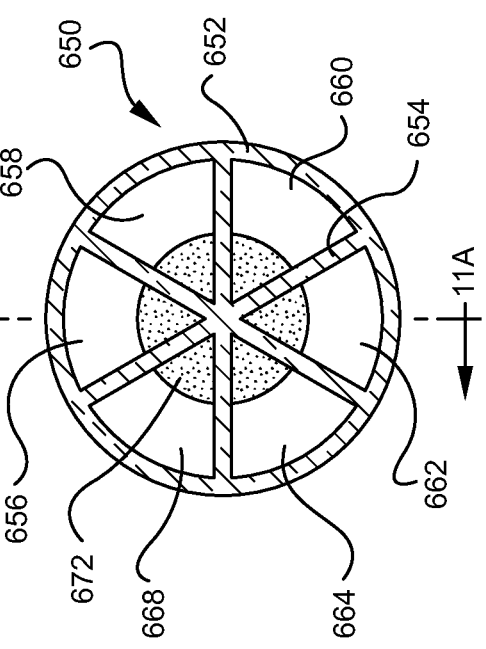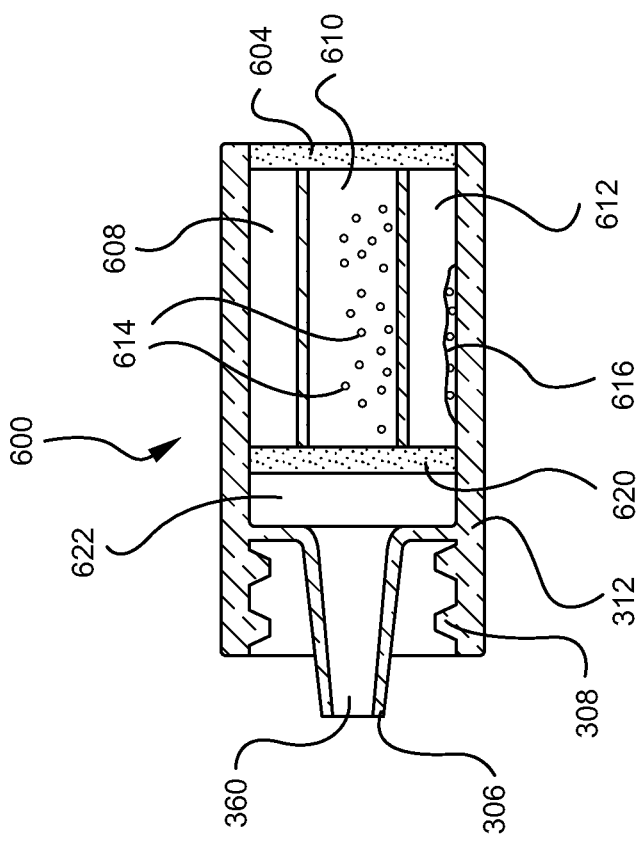

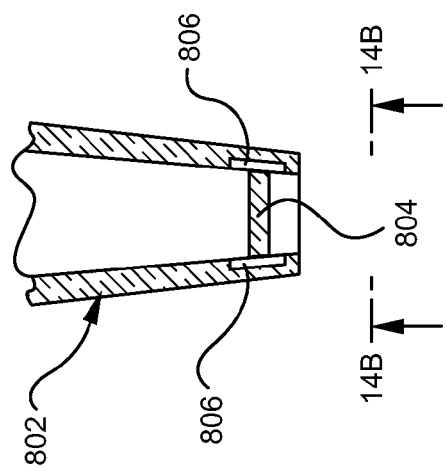
FIG. 12A
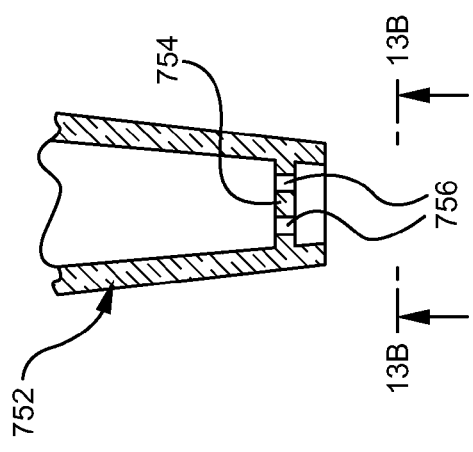
FIG. 13A
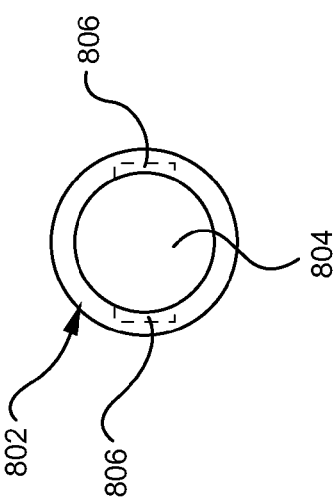
FIG. 14A
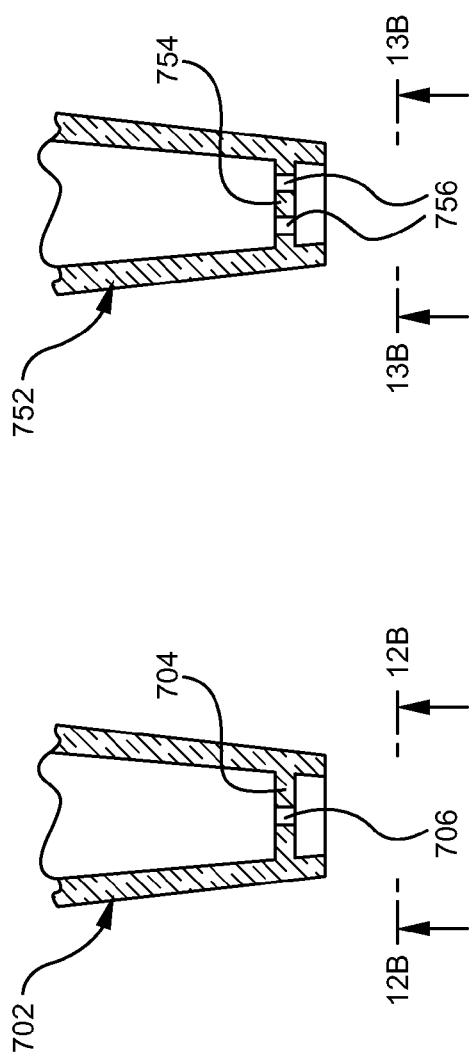
FIG. 12B
FIG. 13B
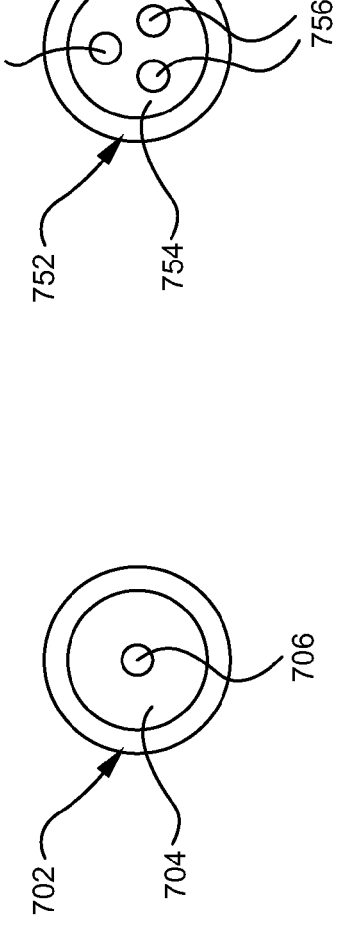
FIG. 14B

BLOOD SAMPLING DEVICE

RELATED APPLICATIONS

This application is a divisional of application Ser. No. 12/831,891, filed Jul. 7, 2010, now U.S. Pat. No. 8,383,044, and entitled BLOOD SAMPLING DEVICE, which claims the benefit of U.S. Provisional Application No. 61/224,208, filed Jul. 9, 2009, entitled CATHETER VENTING, BLOOD SAMPLING AND COLLECTION DEVICE FOR POINT OF USE DIAGNOSTIC TESTING. This application claims priority to and has incorporated herein by reference the utility and provisional application.

BACKGROUND OF THE INVENTION

The present disclosure relates to blood sampling with vascular access devices. Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples are analyzed via one or more blood test levels.

Blood tests determine the physiological and biochemical states of the patient, such as disease, mineral content, drug effectiveness, and organ function. Blood tests may be performed in a laboratory, a distance away from the location of the patient, or performed at the point of care, near the location of the patient. One example of point of care blood testing is the routine testing of a patient's blood glucose levels, which involves the extraction of blood via a finger stick and the mechanical collection of blood into a diagnostic cartridge. Thereafter the diagnostic cartridge analyzes the blood sample and provides the clinician a reading of the patient's blood glucose level. Other devices are available which analyze blood gas electrolyte levels, lithium levels, ionized calcium levels. Furthermore, some point of care devices identify markers for acute coronary syndrome (ACS) and deep vein thrombosis/pulmonary embolism (DVT/PE).

Despite the rapid advancement in point of care testing and diagnostics, blood sampling techniques have remained relatively unchanged. Blood samples are frequently drawn using hypodermic needles, or vacuum tubes coupled to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Furthermore, each device required adds time and cost to the testing process. Accordingly, there is a need for more efficient blood sampling and testing devices and methods.

BRIEF SUMMARY OF THE INVENTION

The present invention has been developed in response to problems and needs in the art that have not yet been fully resolved by currently available blood sampling devices and methods. Thus, these devices, and methods are developed to provide more efficient blood sampling and diagnosis.

The present blood sampling device and method for blood sampling significantly reduce the number of components that are required in order to obtain a diagnostic blood sample immediate after IV insertion. Embodiments of the blood sampling device combines features that obtain, prepare, and directly test blood samples during the normal process of venous access. These embodiments, facilitate the entire blood sampling process for clinicians by reducing the number of process steps and reducing the amount of time between sampling and obtaining test results.

In one aspect, a blood sampling device has a body that is shaped and sized for being partial inserted into a separate vascular access device, such as a catheter, a needle. The body further defines a reservoir within the body, and the reservoir has an internal volume sufficient to contain enough blood for use in a diagnostic blood test. A gas permeable vent is disposed on the body in gaseous communication with the reservoir to enable blood to flow into the reservoir under the force of the patient's blood pressure, as gas flows out the vent.

Implementations may include one or more of the following features. A diagnostic reagent may be disposed within the reservoir. An on-board diagnostic cartridge may be in fluid communication with the reservoir. The body may include a compressible portion that is shaped and sized to eject the contents of the reservoir when compressed. The reservoir may include multiple chambers. When the reservoir includes multiple chambers, at least one of the multiple chambers may include a diagnostic reagent. The reservoir may include a blood preservative. The body may include an indicator of elapsed time since blood sampling. The reservoir may include a distal opening that is in fluid communication with the separate vascular access device when the body is partially inserted into the separate vascular access device. The body may include a male luer adapter shaped and sized for insertion into the separate vascular access device, and the distal opening may be a distal opening of the male luer adapter. The distal opening may include a wicking material disposed therein. The distal opening may include a flow restrictor. The body may include a luer adapter for insertion into the separate vascular access device.

In another aspect, a blood sampling device includes a body shaped and sized for partial insertion into a separate vascular access device. The body defines a reservoir within the body, the reservoir having an internal volume of at least 0.1 µL. A gas permeable vent is disposed on the body, the gas vent in gaseous communication with the reservoir. And a diagnostic component is in fluid communication with the reservoir.

Implementations may include one or more of the following features. The diagnostic component may include an on-board diagnostic cartridge. The diagnostic component may include a diagnostic reagent disposed within the reservoir. The reservoir may include multiple chambers, and at least two of the multiple chambers may include a separate diagnostic component.

In yet another aspect, a blood sampling device includes a body shaped and sized for partial insertion into a separate vascular access device. The body has a compressible portion and a reservoir defined within the body. The compressible portion of the body is shaped and sized to eject at least a portion of the contents of the reservoir when it is compressed. The reservoir has an internal volume of at least 0.1 µL. A gas permeable vent is disposed on the body in gaseous communication with the reservoir. Implementations may include one or more of the following features. The reservoir may have an internal volume of less than 10 mL, or in some embodiments, the internal volume is less than 2 mL. And the reservoir may include a blood preservative.

In still another aspect, a method for blood sampling using a ventable blood sampling device includes inserting a vascular access device into the vasculature of a patient. Next, the method includes inserting a blood sampling device into the vascular access device, the blood sampling device including a body shaped and sized for partial insertion into a separate vascular access device; a reservoir defined within the body, the reservoir having an internal volume sufficient to contain enough blood for use in a diagnostic blood test; and a gas permeable vent disposed on the body, the gas vent in gaseous communication with the reservoir. The method finally includes causing blood to flow from the vasculature of the patient into the blood sampling device to fill the reservoir with blood. Implementations may further include causing to flow by at least one of blood pressure and wicking.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 10 is a cross section view of another blood sampling device having multiple chambers according to a representative embodiment.

FIG. 11A is a cross section view of a blood sampling device having multiple chambers according to a representative embodiment. This cross section is taken along line 11A of FIG. 11B.

FIG. 11B is a cross section view of the blood sampling device of FIG. 11A taken along line 11B of FIG. 11A.

FIG. 12A is a cross sectional view of a distal end of a blood sampling device according to a representative embodiment.

FIG. 12B is an end view of the distal end of the blood sampling of FIG. 12A.

FIG. 13A is a cross sectional view of a distal end of a blood sampling device according to a representative embodiment.

FIG. 13B is an end view of the distal end of the blood sampling of FIG. 13A.

FIG. 13A is a cross section view of a vascular access device and a vent plug.

FIG. 14A is a cross sectional view of a distal end of a blood sampling device according to a representative embodiment.

FIG. 14B is an end view of the distal end of the blood sampling of FIG. 14A.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The present invention relates to a blood sampling device that may collect a blood sample from a variety of extravascular system. FIGS. 1 through 4 illustrate various extravascular systems with which the blood sampling device 102 may be used. It will be understood that the blood sampling device 102 is not limited to these illustrated system, but may be used with other extravascular systems, ranging from a simple needle, to more complex extravascular devices. From these figures it is apparent that a blood sampling device 102 may reduce the number of components required to draw a diagnostic blood sample from a patient. This is because the blood sampling device combines blood collecting, storing, and testing features into a single device.

Figure 1:
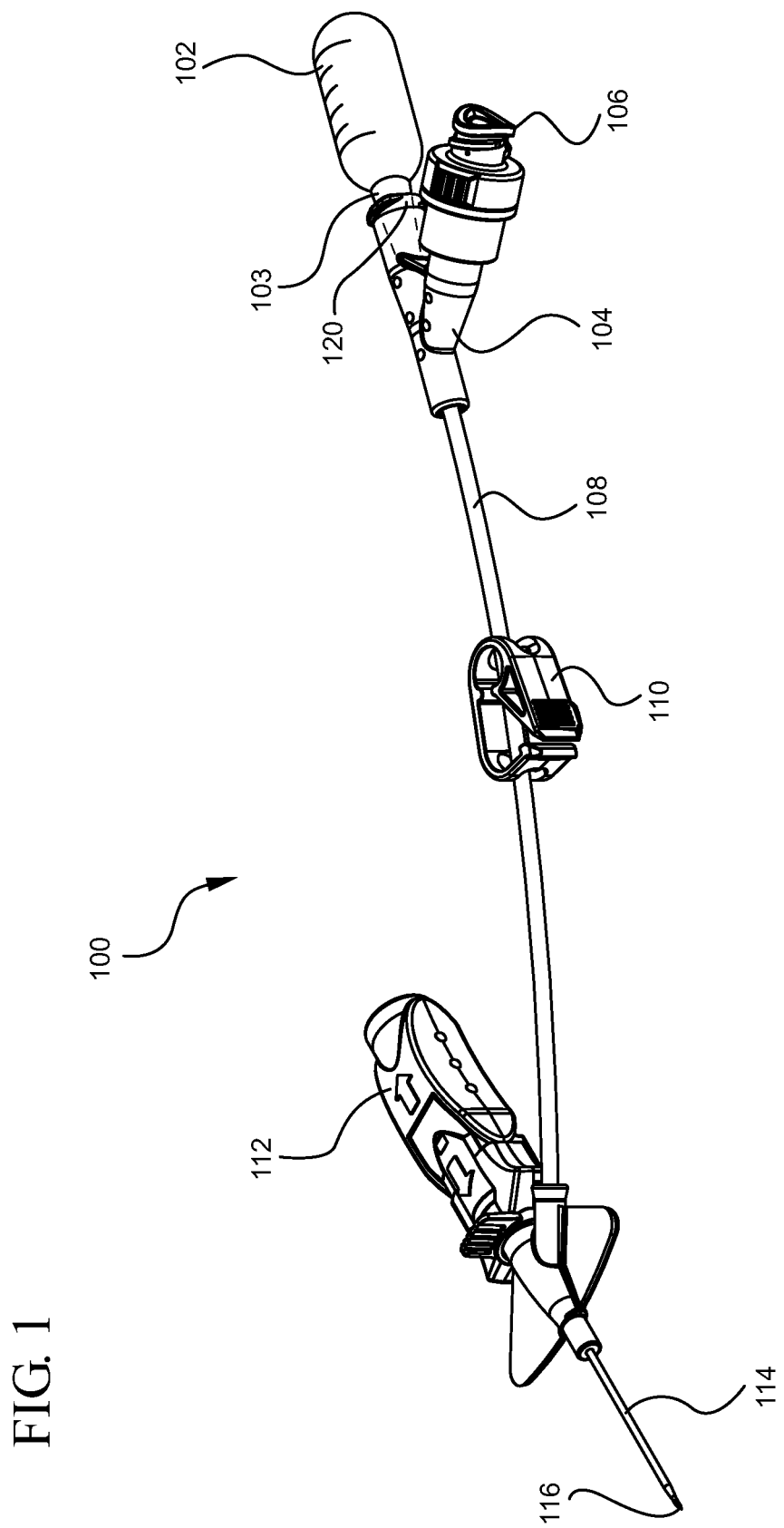
FIG. 1 is a perspective view of an extravascular system of vascular access devices and a blood sampling device according to a representative embodiment.

Referring now to FIG. 1, an extravascular system 100, such as the BD NEXIVA™ Closed IV (intravenous) Catheter System, by Becton, Dickinson and Company, may be accessed using a blood sampling device 102. An example of the system 100, as shown in FIG. 1, includes multiple vascular access devices such as an intravascular needle 116; an over-the-needle, peripheral intravascular catheter 114; an integrated extension tubing 108 (also referred to herein as a catheter) with a Y adapter 104 having two ports 120 and clamp 110; a Luer access device or port 106; and a passive needle-shielding mechanism 112. Any adapter used to connect two or more vascular access devices may be used in place of the Y adapter 104.

Figure 2:
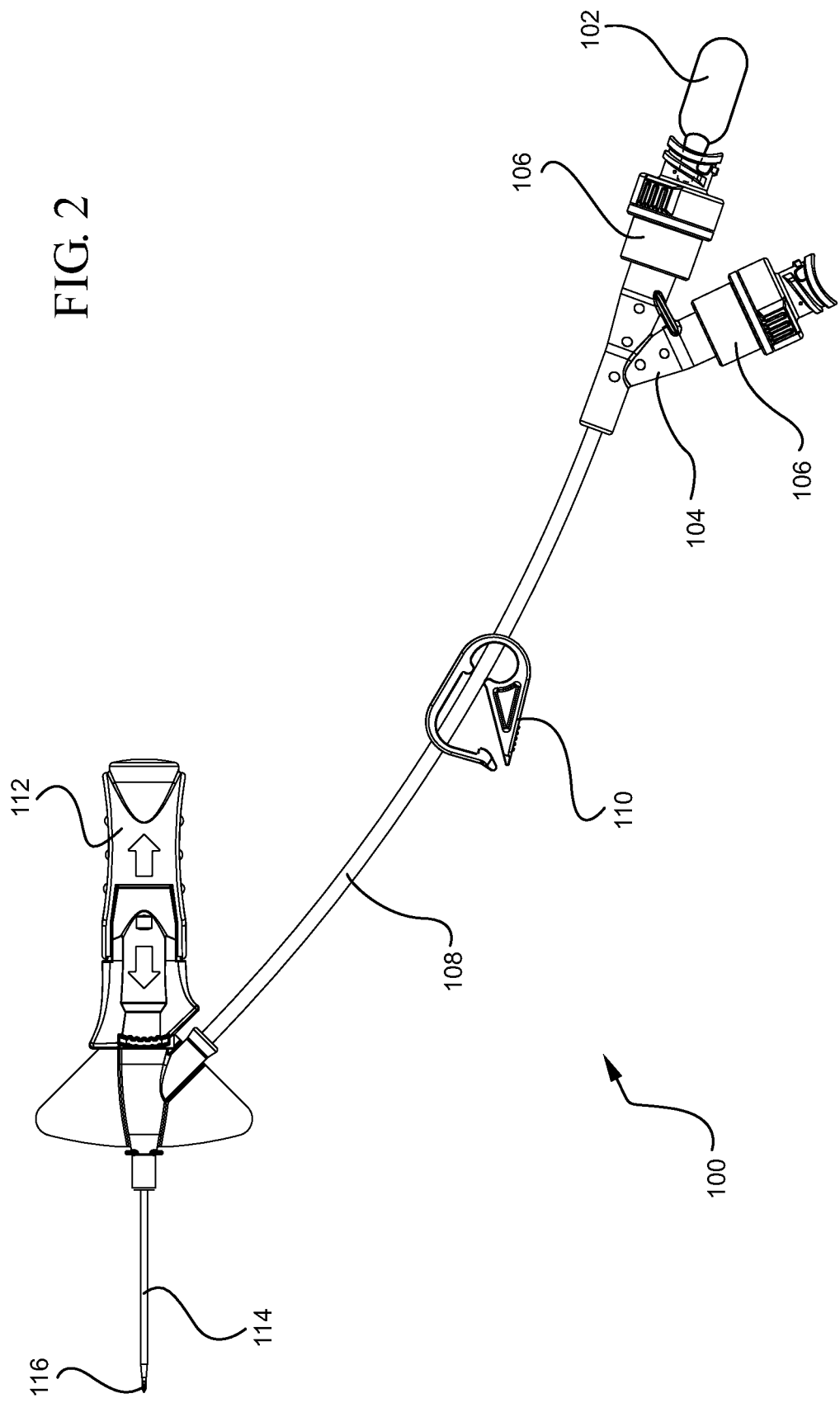
FIG. 2 is a top perspective view of another extravascular system of vascular access devices and a blood sampling device according to a representative embodiment.

As shown, a blood sampling device 102 may be inserted into a port 120 of the Y adapter 104 to collect a blood sample therefrom. Alternatively, as shown in FIG. 2, in some embodiments, the blood sampling device is inserted into a Luer access device rather than directly into the port 120 of the Y adapter 104. As shown, in some embodiments, the blood sampling device 102 has a distal end that is shaped and sized for insertion into a separate vascular access device, such as a Luer access port. In some embodiments, the distal end is a male coupler. In some embodiments, the distal end is a male luer connector.

After the introducer needle 116 is withdrawn from the extravascular system 100 both ports of the Y adapter 104 are closed. At this point blood is contained within the system 100. The clamp 110 on the integrated extension tubing 108 may then selectively limit or eliminate blood flow to the blood sampling device 102. As the clamp 110 opens the extension tubing 108, blood flows into the blood sampling device 102 to fill the internal reservoir with enough blood for an adequate blood sample. Generally, an adequate blood sample includes between 0.1 μL-200 mL of blood.

Figure 3:
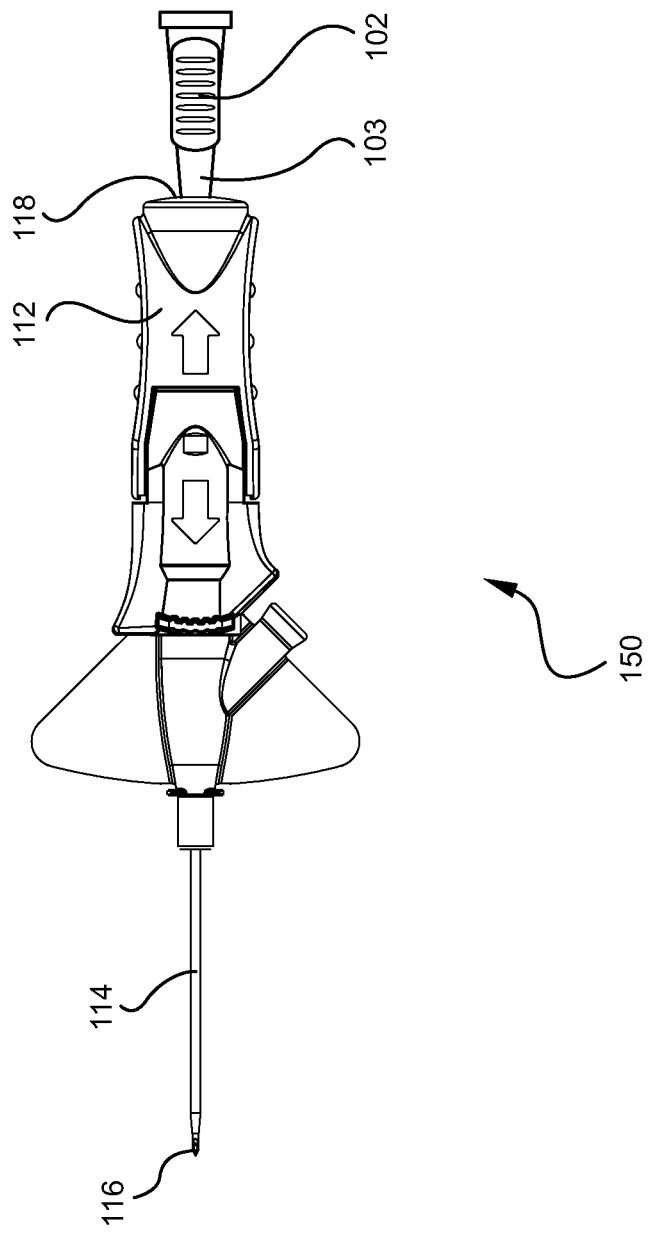
FIG. 3 is a perspective view of another extravascular system of vascular access devices and a blood sampling device according to a representative embodiment.

FIG. 3 depicts an alternative extravascular system 150 that is accessed by a blood sampling device 102 directly at a proximal end rather than through an extension tube. The extravascular system 150 includes an intravascular needle 116; an over-the-needle, peripheral intravascular catheter 114, and a passive needle-shielding mechanism 112. The proximal end of the needle-shielding mechanism includes a port 118 through which a blood sampling device 102 is inserted. Once inserted, the blood sampling device 102 can receives a blood sample from a patient, as blood flows through intravascular catheter 114 and into the internal reservoir of the blood sampling device 102.

Figure 4:
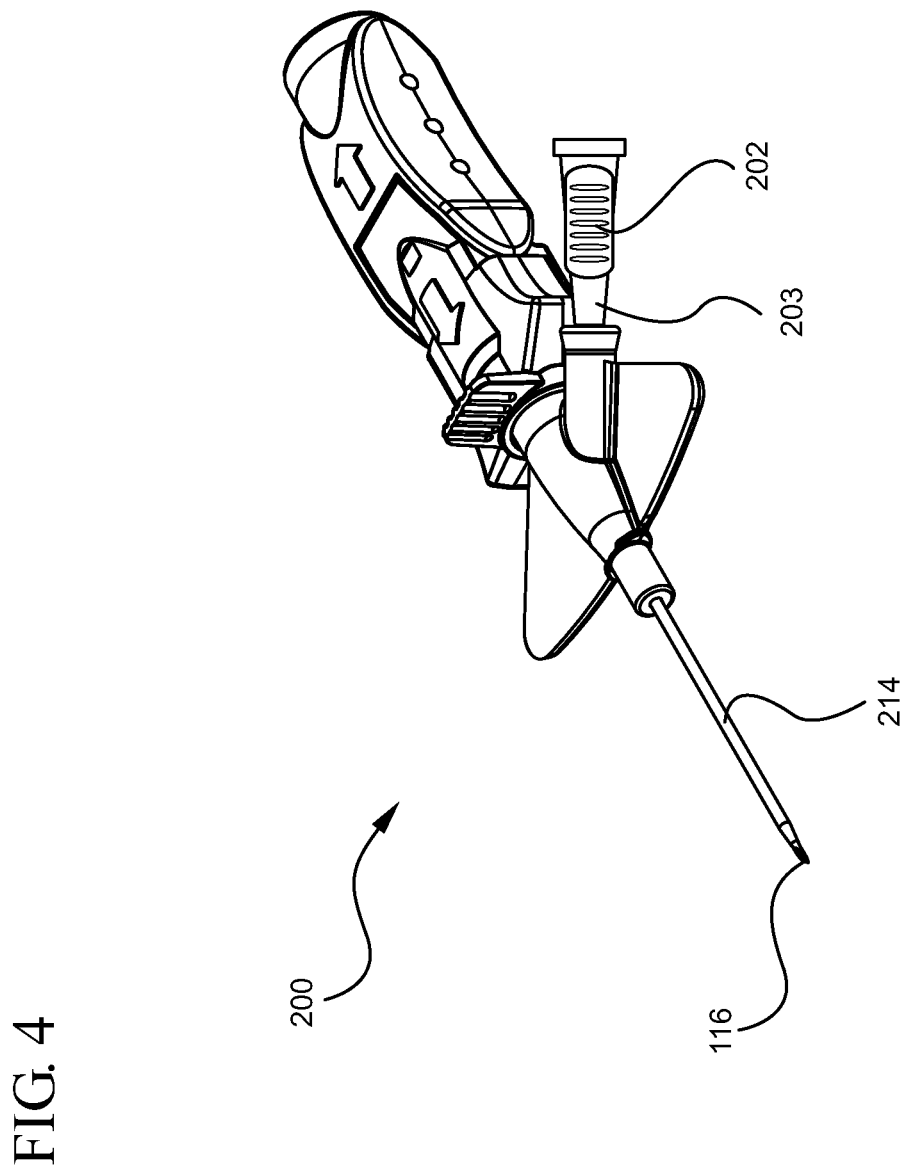
FIG. 4 is a perspective view of another extravascular system of vascular access devices and a blood sampling device according to a representative embodiment.

Referring now to FIG. 4, another alternative extravascular system 200 is depicted that is accessed by a blood sampling device 202 to obtain a blood sample. The extravascular system 200 is used to communicate fluid with the vascular system of a patient. Once the introducer needle 116 is withdrawn from the extravascular system 200, the distal end 203 of a blood sampling device 202 is inserted into the extravascular system 200 to draw blood through the catheter 214 and into the blood sampling device 202. In some embodiments, an extravascular system 200 has an interior cavity (not shown) and the blood sampling device 202 is inserted into the cavity in order to access the extravascular system 200.

Upon inserting into an open extravascular system, the blood sampling device 102 draws blood therein. In some embodiments, blood flows into the blood sampling device 102 under venous pressure. Referring back to FIG. 1, in some embodiments, the blood sampling device 102 has a gas permeable vent (shown in FIG. 5) disposed thereon to permit a patient's venous pressure to cause blood to flow through the extravascular system 100 to the blood sampling device 102. As blood enters the system 100, the gas permeable vent permits air to escape from the blood sampling device 102, drawing blood therein. Accordingly, a gas permeable vent enables the blood sampling device to be powered entirely by the patient's blood pressure.

In other embodiments, blood is drawn into the blood sampling device using, at least in part, other power sources. For examples, in some embodiments, the blood sampling device is a vacuum tube that draws blood therein using vacuum force. In other embodiments, blood is drawn into the blood sampling device using a pump or a syringe. In other embodiments, the blood sampling device receives blood via a wicking means disposed within the distal end of the blood sampling device. In some embodiments, the wicking material comprises micro fluidics.

After the blood sampling device collects an appropriate blood sample, the sample can be analyzed. With continued reference to FIG. 1, the clamp 110 stops blood flow to the Y adapter 104 and the blood sampling device 102 so that the blood sampling device can be removed from the extravascular system 100. In some instances, the blood sampling device 102 will be sent to a laboratory for analysis. In some embodiments, the body of the blood sampling device is at least partially compressible and blood will be squeezed out for testing, even point of care testing. In other embodiments, the blood sampling device 102 includes a diagnostic reagent that enables diagnostic tests to be conducted within the blood sampling device 102. In yet other embodiments, the blood sampling device 102 includes an on-board diagnostic cartridge that analyzes the blood sample and displays an analysis result on the on-board diagnostic cartridge. These various embodiments will be described in detail below.

Figure 5:
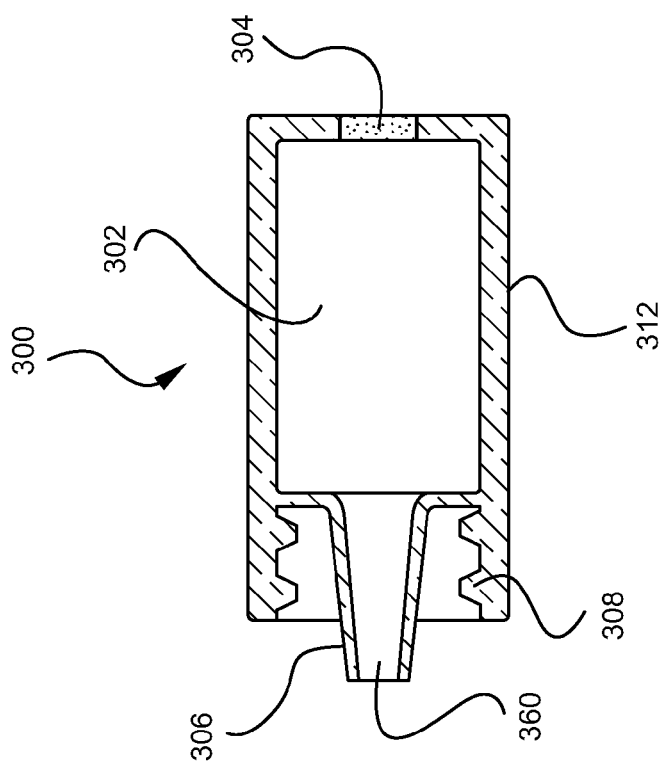
FIG. 5 is a cross section view of a blood sampling device according to a representative embodiment.

Referring now to FIG. 5, a cross section of a blood sampling device 300 is depicted, which illustrates a body 312 defining an internal reservoir 302. The body 312 and reservoir 302 can have a variety of shapes and sizes. In some embodiments, the reservoir has a volume of at least 0.1 μL-10 mL, corresponding to a standard volume for a blood sample, or a single drop of blood. In some embodiments, the reservoir volume is up to 200 mL. A 200 mL reservoir volume may be capable of containing a large enough blood sample for multiple different blood tests. In other embodiments the reservoir volume is less than 20 mL or greater than 200 mL.

In some embodiments, the body 312 is shaped and sized for insertion into an extravascular system, as previously discussed. In some embodiments, the distal end of the body includes a male coupler 356 in the form of an elongate stem or cannula, such as the shown in FIGS. 6A-7C, which is selectively inserted into a separate vascular access device. In some embodiments, the male coupler is a male luer connector. As shown, the distal end of the body 312 comprises a male luer connector having threads 308 and a male coupler 306. This distal end is shaped and sized for at least partial insertion into a separate vascular access device, such as a luer adapter 106, a Y adapter 104, a catheter assembly, a catheter nub, a needle hub, a needle, a catheter, or other vascular access device, such as those shown in FIGS. 1-4.

As discussed above, in some embodiments, a gas permeable vent 304 is disposed on the body 312 to allow airflow to pass therethrough and to prevent fluid, such as blood from passing therethrough. This gas permeable vent 304 is in fluid communication with the reservoir 302. The vent may be hydrophobic or hydrophilic and may be a glass, polyethylene terephthalate (PET), a microfiber material, or other synthetic material made of high-density polyethylene fibers, such as TYVEK® material from DuPont. As shown, the gas permeable vent 304 is disposed on a proximal end of the body 312. However, in other embodiments, the gas permeable vent 304 is located on other surfaces or portions of the body 312. For instance, in some embodiments, the gas permeable vent 304 is disposed on a side of the body. Furthermore, more than one gas permeable vent 304 can be disposed on the body 312. For instance, when more than one chamber is included in the reservoir 302, each chamber can have a separate gas permeable vent 304.

Figure 6A:
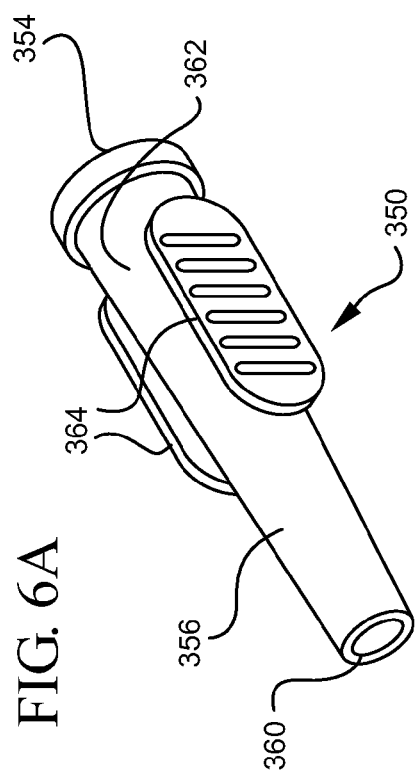
FIG. 6A is a perspective view of a blood sampling device according to a representative embodiment.

FIG. 6A illustrates a perspective view of a blood sampling device 350 having a body with a compressible body portion 362. As used herein the term "compressible" refers to any means to reduce the size of the reservoir volume in order to eject a sample of fluid within the reservoir. For example, the compressible portion may include an entire flexible body with the exception of the male coupler 356, or the compressible portion may be limited to a limited portion of the body, which flexes when the more rigid portions are compressed together. In other instances, the compressible portion includes a plunger disposed on the body and which forms part of the reservoir. The plunger (not shown) may respond to an external inward force by moving inward within the body to decrease the internal volume of the reservoir, thus ejecting a blood sample. In some embodiments, to facilitate compression, the body includes two opposing grips or pads 364 that facilitate gripping and compressing the body. The pads 364 may be rigid or compressible.

Figure 6B:
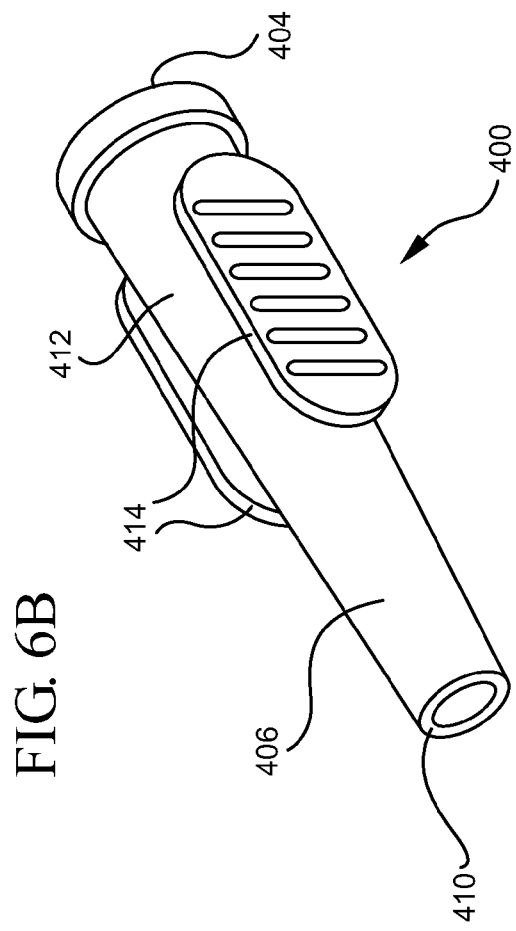
FIG. 6B is a perspective view of another blood sampling device according to a representative embodiment.

Because different blood tests required different quantities of blood, in some embodiments, the reservoir is sized to retain a quantity of blood needed for a specific blood test or for a specific number of blood tests. In some embodiments, a set of blood sampling devices is provided to a clinician having multiple blood sampling devices of different sizes. Accordingly, FIGS. 6A and 6B illustrate a smaller blood sampling device 350 and a larger blood sampling device 400. These devices 350 and 400 include a male coupler 356 and 406, a compressible body portion 362 and 412, pads 364 and 414, a gas permeable vent 354 and 404, and a distal lumen 360 and 410. Hereinafter, to simplify the description, reference will be made only to the embodiment of FIG. 6A.

Figure 7A:
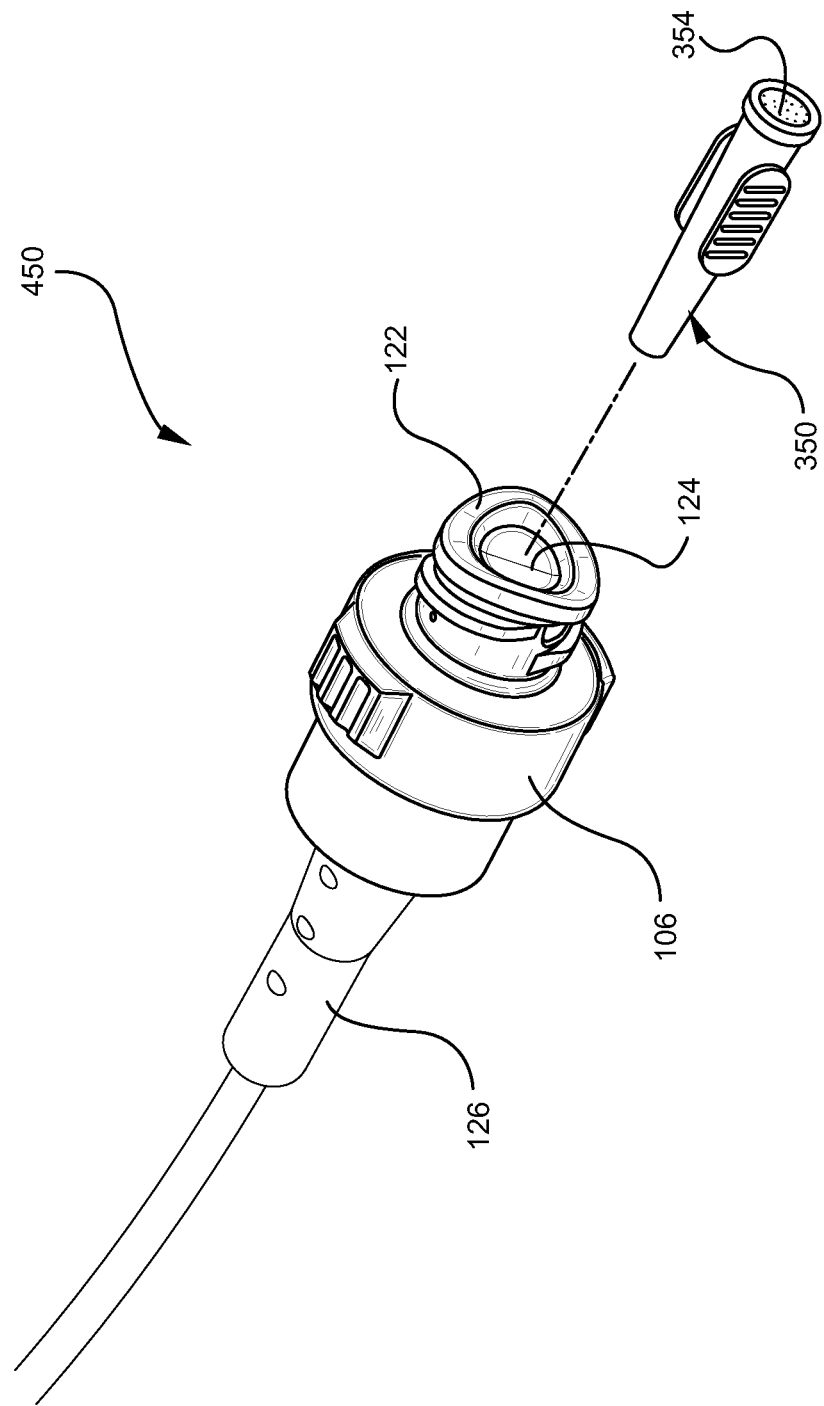
FIG. 7A is a perspective view of an extravascular system of vascular access devices and a blood sampling device in use according to a representative embodiment.
Figure 7B:
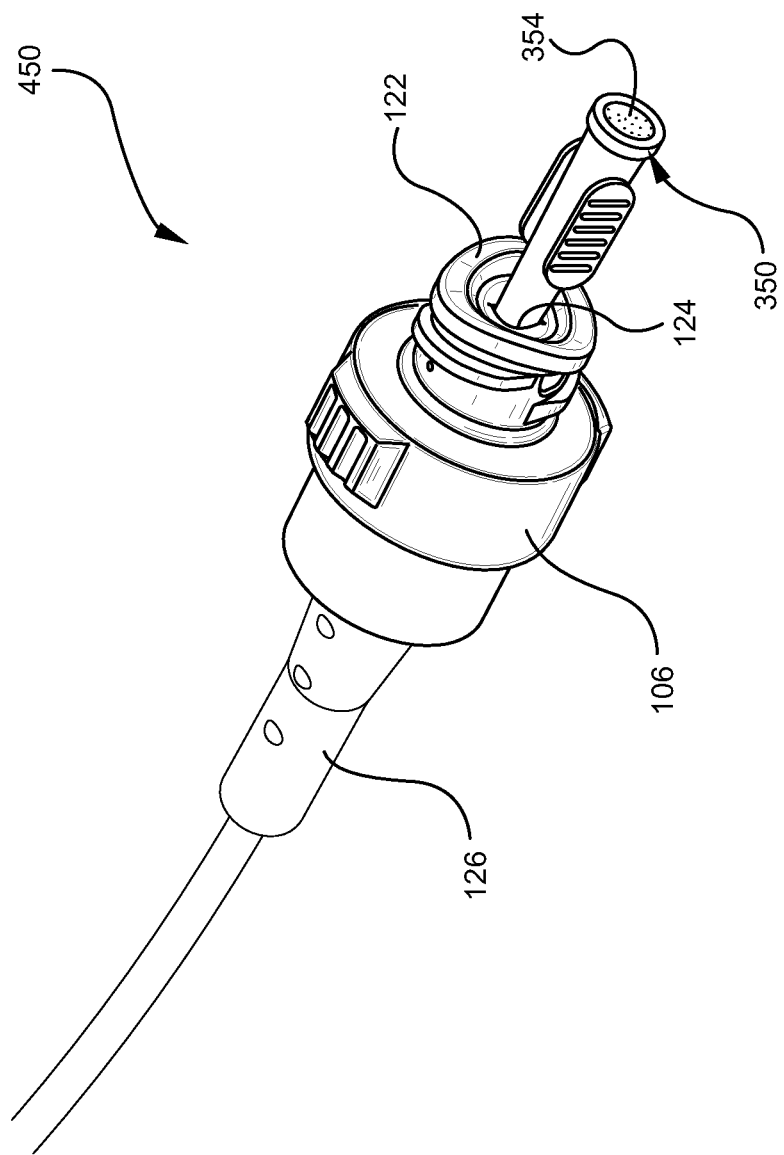
FIG. 7B is a perspective view of an extravascular system of vascular access devices and a blood sampling device in use according to a representative embodiment.
Figure 7C:
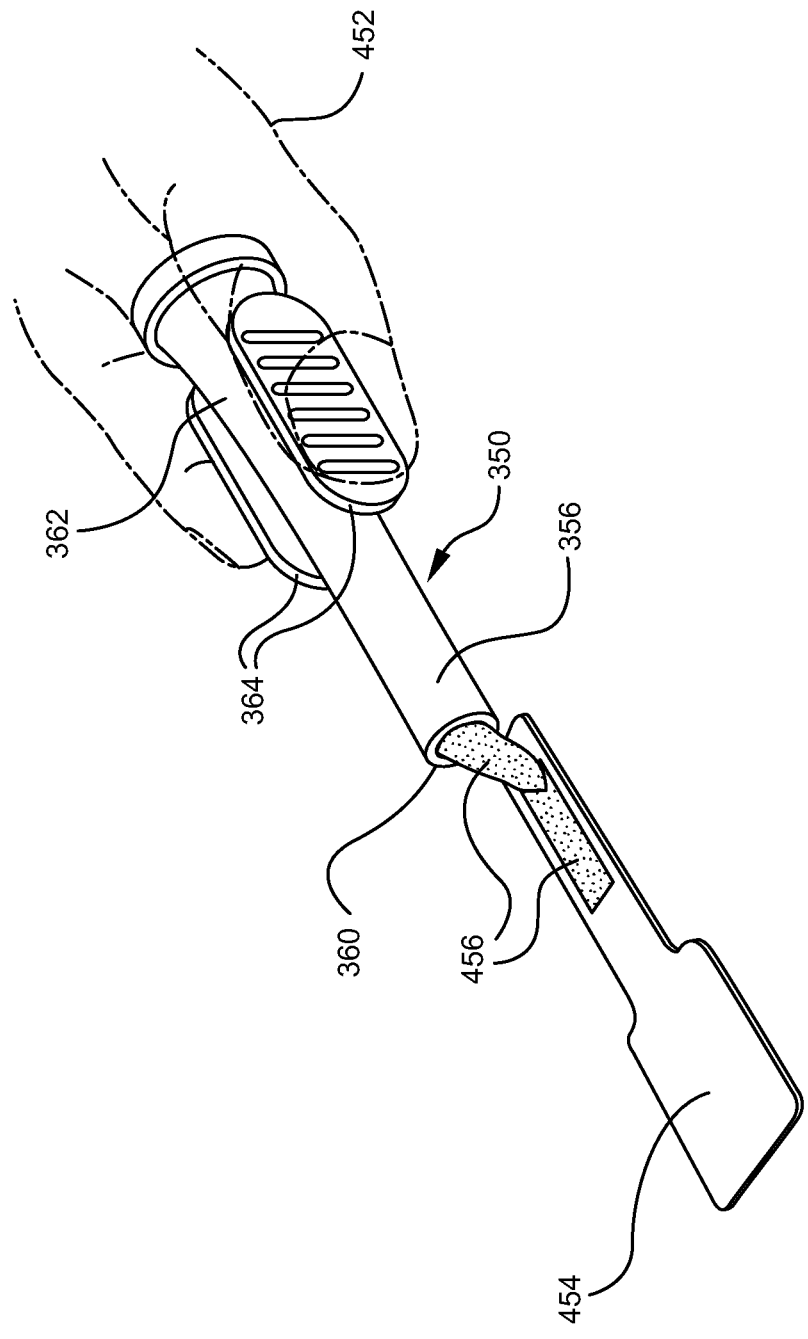
FIG. 7C is a perspective view of a test strip and a blood sampling device in use according to a representative embodiment.

FIG. 7A-7C, illustrates the process of sampling and testing blood using a blood sampling device 350 having a compressible body portion 364. In operation, as shown in FIGS. 7A-7B, the male coupler 356 of blood sampling device 350 is selectively inserted into a separate vascular access device 450. For example, a separate vascular access device 450 is illustrated having an adapter 126, and a luer adapter 106 with a septum 122 having a slit 124. When the male coupler 356 is inserted into the septum 122, the reservoir 302 of the blood sampling device is in fluid communication with the separate vascular access device 450 and thus the vasculature of a patient. As blood flows through the separate vascular access device 450 towards the blood sampling device gas exits the through the gas permeable vent 354 of the blood sampling device 350. In this manner, blood flows into the blood sampling device and fills the reservoir 302.

As shown in FIG. 7C, once blood is received into the reservoir 302, the blood sampling device 350 can be removed from the separate vascular access device and compressed by a clinician 452 such that the blood sample 456 is partially or entirely expelled from the reservoir. The blood sample may be expelled onto a test strip 454 (as shown), into a diagnostic cartridge, or retained within the blood sampling device 350 and transported to a laboratory for analysis.

In some embodiments, the body has no compressible portion, but is rigid. As such, to extract the blood sample, in some embodiments a wicking means is inserted into the blood sampling device and wicked therefrom. In other embodiment, blood is merely poured out of the distal opening of the blood sampling device. In other instances, the gas permeable membrane is pierced to enable blood to flow out the distal opening. In still other embodiments, blood is withdrawn with a needle and syringe.

Figure 8:
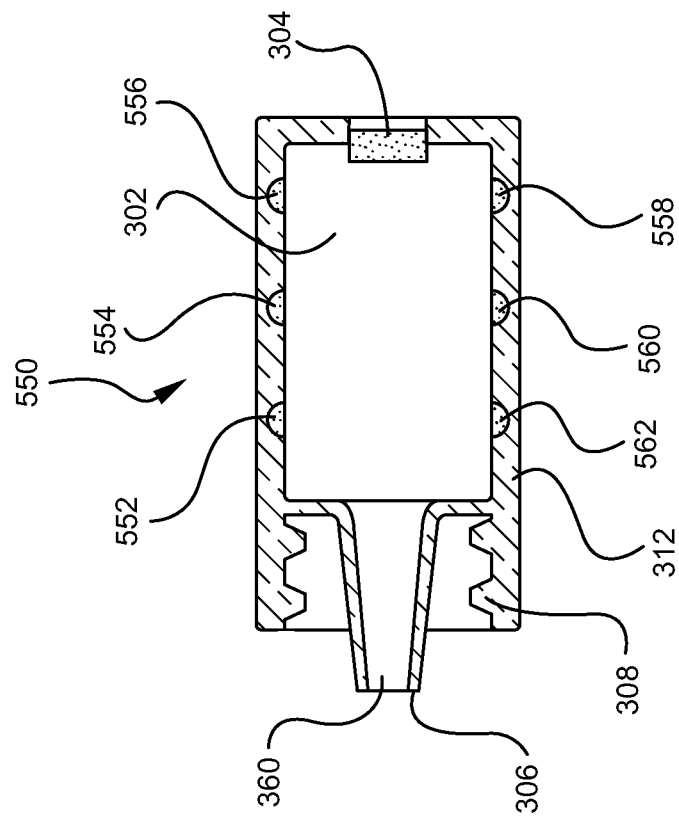
FIG. 8 is a cross section view of a blood sampling device according to a representative embodiment.

Since some blood samples may not be immediately tested, in some embodiments the blood sampling device contains one or more preservative within the reservoir 302 to preserve the blood for later testing. Referring now to FIG. 8, a cross section view of a blood sampling device 500 is shown having one or more preservative 512 contained within the reservoir 302. As blood enters the reservoir it mixes with the preservative. Various preservatives maybe included in the reservoir 302. For example, ethylenediaminetetraacetic acid (EDTA) may be disposed within the reservoir 302 to chelate calcium in the blood and prevent clotting. If clotting time is to be tested then citrates may be included instead of EDTA used. In other embodiments, heparin is included within the reservoir 302. In still other embodiments, other preservative types are included inside the reservoir.

Furthermore, in some embodiments, the blood sampling device includes a time indicator 520 that provides an indication to the clinician or laboratory technician the amount of time has elapsed since the sample was taken. In some embodiments, the time indicator 520 is external to the reservoir, such as a color changing sticker that changes color based on elapsed time and/or temperature. In other embodiments, the time indicator 520 is a time stamp. In other embodiments, the time indicator 520 indicates the passage of time in which the blood sample is no longer useful, such as an expiration time. In some embodiments, the time indicator 520 is disposed within the reservoir and is activate by contact with the blood sample.

Figure 9:
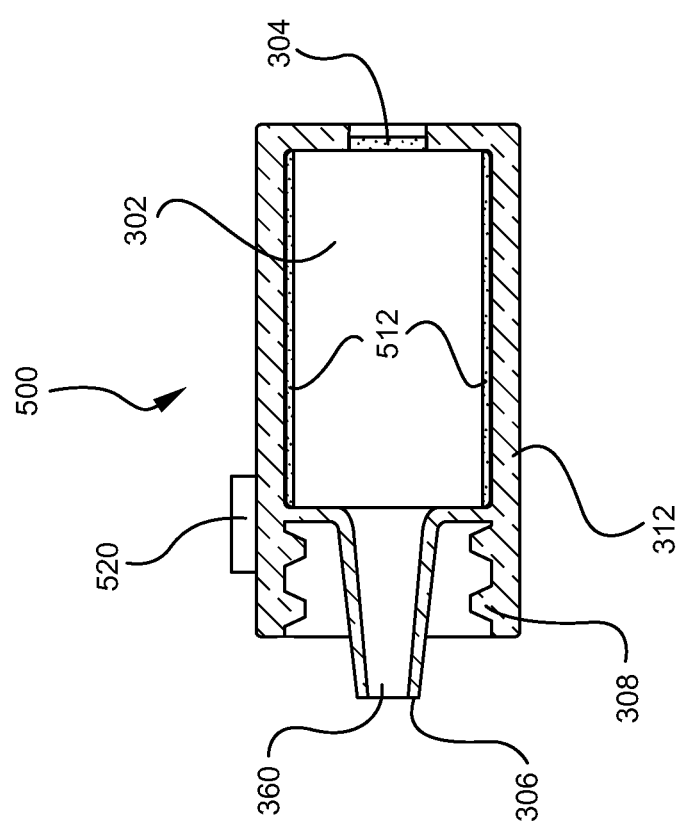
FIG. 9 is a cross section view of another blood sampling device having one or more diagnostic reagents according to a representative embodiment.

Additionally or alternatively, the blood sample can be tested within the blood sampling device. In some embodiments, the reservoir includes one or more diagnostic reagent disposed within the reservoir 302 that reacts with the blood sample and provides a visual indication to the clinician. Diagnostic reagents can indicate a patient's physiological and biochemical states, such as disease, mineral content, drug effectiveness, and organ function. Referring now to FIG. 9, in some embodiments, the reservoir 302 includes one or more diagnostic reagent 552, 554, 556, 558, 560, and 562, each of which may test for a different physiological and/or biochemical state. For example, in one embodiment, a reservoir may include eight diagnostic reagents, each of the reagents measure one of the elements of the basic metabolic panel: sodium, potassium, chloride, bicarbonate, blood urea nitrogen (BUN), magnesium, creatinine, and glucose. In some embodiments, the reagents may provide a visual result, such as a color change. In other embodiments the reagents provide a non-visual result, which may be read by a machine or processed in a laboratory. For clarity of use, the exterior of the blood sampling device body 312 may be transparent or semi-transparent and include markings that indicate the type of reagent disposed near the marking. In this manner, the blood sampling device 600 may provide a point of care diagnostic tool to clinicians.

In some embodiments, different diagnostic reagents are kept separate to enable more accurate results. Accordingly, as shown in FIG. 10, in some embodiments, the reservoir 622 includes multiple chambers 608, 610, 612, separated by divider portions of the body, such that one or more of the chambers includes a reagent 614 and 616. Additionally, in some embodiments, one or more chamber may include a preservative. Since each chamber 608, 610, 612 is in fluid communication with the gas permeable vent 604 blood flowing into the reservoir 622 flows into each of the chambers 608, 610, 612. As blood enters the chambers 608, 610, 612 it mixes with any reagents therein. Once mixed, the reagents may provide diagnostic information to a clinician without the need for additional tools or further delays.

In some embodiments, the reservoir chambers 608, 610, 612 are also separated by a distal flow restrictor 620. The flow restrictor 620 limits fluid communication between each chamber by limiting the speed at which fluid passes therethrough. Accordingly, once blood passes through the filter and mixes with the reagent it is partially limited by the flow restrictor 620 from exiting the chamber and entering another reservoir chamber by the flow restrictor 620. In some embodiments, the flow restrictor includes a continuous, porous filter that spans the reservoir cross section and limits the speed at which fluid passes therethrough. Alternative examples of flow restrictors are illustrated in FIGS. 12A-14B. To prevent unnecessary blood exposure in each container, a clinician may set the blood sampling device upright on its proximal end (the end illustrated as having the gas permeable vent 604) during the time of the reagent's reaction process(es). Alternatively, in some embodiment, the blood sampling device 550 includes a cap that covers the distal opening and prevents blood exposure.

FIGS. 11A-11B illustrate an alternative reservoir chamber configuration. In some embodiments, the reservoir is divided into multiple chambers 656, 658, 660, 662, 664, and 668, separated by radial divider portions 654 of the body 652. In some embodiments, each chamber is in fluid communication with a gas permeable vent 672. In other embodiments, as discussed above, each of the chambers is in fluid communication with a separate gas permeable vent (not shown). Accordingly, in some embodiments, the body includes two or more gas permeable vents.

In some embodiments, the divider portions 654 of the body 652 extend distally to the male coupler 306. In other embodiments, the divider portions 654 of the body 652 extend into the male coupler 306, such that fluid is segregated into the various chambers immediately upon entry into the blood sampling device 650. In still other embodiments, the divider portions 654 of the body 652 extend only partially into the male coupler 306. In yet other embodiments, the divider portions 654 of the body 652 do not extend all the way to the male coupler 306, but extend only partially between the proximal and the distal ends of the reservoir 302, similar to that shown in FIG. 10. Furthermore, in some embodiments, the entry to the chambers includes a flow restrictor 620, such as that shown in FIGS. 10 and 12A-14B, to form a partial barrier to the chambers.

Referring now to FIGS. 12A-14B, in some embodiments, the distal end of the blood sampling device includes a flow restrictor that comprises a solid barrier 704 formed integrally with the body. The solid barrier 704 includes one or more holes or channels therethrough to enable some fluid flow into the blood sampling device. The one or more holes may retain the fluid within the reservoir via surface tension alone. For example, FIGS. 12A-12B illustrate a flow restrictor comprising a solid barrier 704 having a single hole 706 therethrough. The hole 706 may be shaped and sized to resist blood flow therethrough absent venous pressure. In some embodiments the hole has a diameter within the range of 0.1 to 0.5 mm. In other embodiments the hole has a diameter within the range of 0.2 to 0.3 mm. Accordingly, in operation, venous pressure will cause blood to flow in the blood sampling device. Once inside the internal reservoir, the blood will not generally flow out the hole of the flow restrictor absent additional pressure. The holes or channels may be cut or molded into the flow restrictor.

Referring now to FIGS. 13A-13B, in some embodiments, a flow restrictor 754 is a solid barrier having a plurality of holes 756 therethrough. Multiple holes 756 may increase the rate of flow through the flow restrictor 754. Additionally, in some embodiments, the flow restrictor 754 includes a hole for each internal chamber so that each hole directs fluid to a separate chamber. As such the flow restrictor may form a distal barrier to each internal chamber.

In some embodiments, a flow restrictor is disposed within the male coupler 702. Thus positioned, as the blood sampling device is removed from the separate vascular access device the flow restrictor prevent exposure to blood otherwise within the male coupler 702. In other embodiments, the flow restrictor is disposed with the reservoir of the blood sampling device, as explained above.

Referring now to FIG. 14A-14B, in some embodiments, the flow restrictor comprises a solid barrier 808 spanning the male coupler 802, and one or more channels 806 molded or cut into the male coupler 802. In some embodiments, the cut-out channels 806 have lengths and widths within the range of 0.1 to 0.5 mm. These channels function like the holes described with reference to FIGS. 12A-13B, to enable blood entry into and limit blood removal from the blood sampling device.

Figure 15:
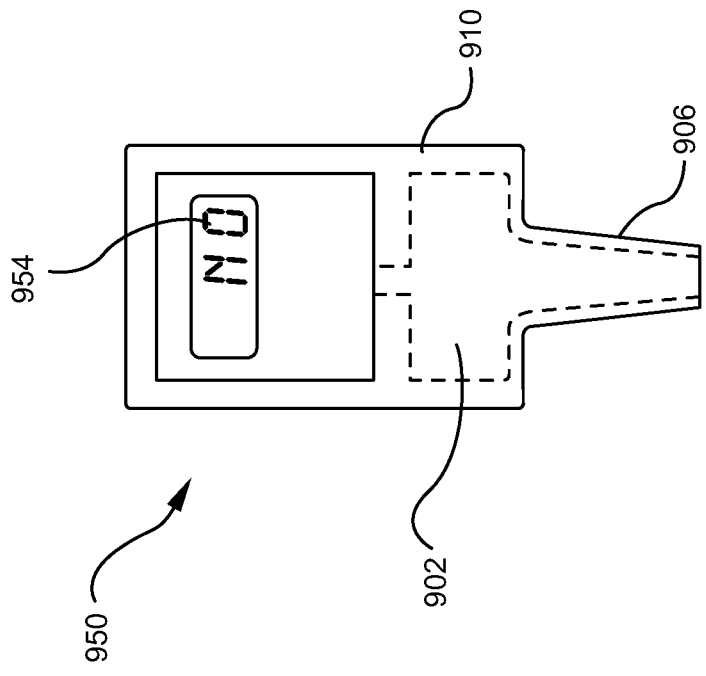
FIG. 15 is a top view of a blood sampling device having an on-board diagnostic cartridge according to a representative embodiment.
Figure 16:
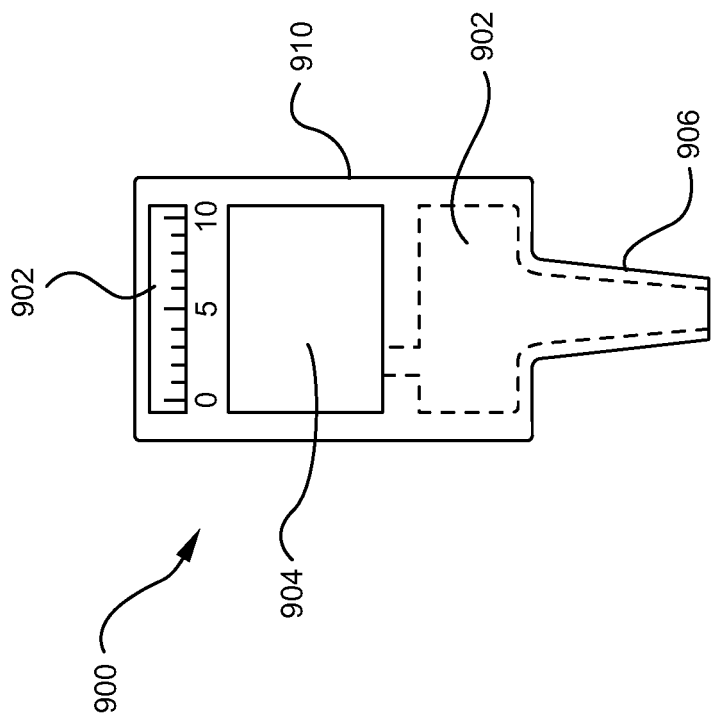
FIG. 16 is a top view of another blood sampling device having an on-board diagnostic cartridge according to a representative embodiment.

Reference will now be made to FIGS. 15 and 16, which illustrate a blood sampling device having an on-board diagnostic cartridge. Diagnostic cartridges are point of care diagnostic device that receive a blood sample and test that blood for one or more physiological and biochemical states. Due to their small size diagnostic cartridges may be used at the point of care, thus providing clinicians and patients rapid test results. After testing is complete the on-board diagnostic cartridge displays one or more test result to the clinician. Accordingly, the clinician receives test results within minutes of taking a blood sample. Examples of on-board diagnostic cartridges include the i-STAT® testing cartridge from the Abbott group of companies. These devices may include displays similar to those used in digital, disposable pregnancy tests that employ display technologies, and are relatively economical (e.g. Clearblue Easy Digital Pregnancy Test from Clearblue).

On-board diagnostic cartridges, thus, enable a clinician to receive electronic analysis of a blood sample at the point of care and in a relatively short period of time. Referring now to FIGS. 15 and 16, in some embodiments, a blood sampling device 900 and 950 comprises a body 910 defining an internal fluid reservoir 902 and having a male coupler 906. The blood sampling device 900 further includes an on-board diagnostic cartridge 904 having a display 902. The on-board diagnostic cartridge 904 receives blood via a fluid communication channel or direct contact with the reservoir 902. Thus, blood within the reservoir is communicated to the on-board diagnostic cartridge 904 and analyzed therein.

In some embodiments, the on-board diagnostic cartridge 904 is integrated into the body 910 of the blood sampling device 900. In other embodiments, the on-board diagnostic cartridge 904 is selectively coupled to the body 910 and selectively removable from the body 910. Accordingly, in some embodiment the body 910 includes a slot, latch, clip, or channel for receiving a selectively removable on-board diagnostic cartridge 904.

As stated above, the on-board diagnostic cartridge 904 employs internal analysis capabilities. Thus, in some embodiments, the on-board diagnostic cartridge 904 includes an internal circuit board; a power source, such as a battery; and appropriate components necessary to separate the blood into components and analyze the blood. To display the results of the analysis the on-board diagnostic cartridge 904 includes a display. In some embodiments, the display is a LCD display 954 (shown in FIG. 16). In other embodiments, the display is a color changing structure that changes color to indicate the result of the analysis.

The blood sampling device having an on-board diagnostic cartridge 904 combines features of medical technology that obtain, prepare, and directly test blood samples into a single, easy to use device. Such a device reduces the number of process steps and reduces the amount of time between sampling and obtaining test results.

From the foregoing it will be seen that a blood sampling device can be utilized to collect a blood sample from a patient. Accordingly, a method for blood sampling using a ventable blood sampling device involves, first, inserting a vascular access device into the vasculature of a patient. As illustrated in FIGS. 1-4, the blood sampling device is shaped and sized to be partially inserted into a variety of vascular access devices, including catheters, needle tips, and other devices having a female luer connection.

Next, the blood sampling device is inserted into the vascular access device. In some embodiments, the blood sampling devices includes a distal male coupler of the body of the blood sampling device includes a threaded male luer connector. In other embodiments, the distal male coupler comprises a projection having an interior lumen, but has no threads.

Lastly, blood is caused to flow from the vasculature of the patient into the blood sampling device to fill the reservoir of the blood sampling device with blood. In some embodiments, blood flow into the reservoir is powered by venous pressure from the patient, and facilitated by the inclusion of a gas permeable vent in fluid communication with the reservoir. As venous pressure forces blood into the reservoir, the gas permeable vent allows gases within the reservoir to escape through the vent. In other embodiments, blood flow into the reservoir is powered by a vacuum within the reservoir. In still other embodiments, blood flow into the reservoir is powered by a syringe coupled to the body of the blood sampling device.

Thus, the present blood sampling device and method for blood sampling significantly reduce the number of components that are required in order to obtain a diagnostic blood sample immediate after IV insertion. As described herein, embodiments of the blood sampling device may combines features that obtain, prepare, and directly test blood samples during the normal process of venous access. These embodiments, facilitate the entire blood sampling process for clinicians by reducing the number of process steps and reducing the amount of time between sampling and obtaining test results.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A blood sampling device, comprising:
a body having an exterior wall forming a proximal end, a distal end, and a distal opening, the distal end being configured for coupling with a separate vascular access device;
a reservoir, defined by the exterior wall of the body, the distal opening comprising an opening of the reservoir, an inner surface of the exterior wall defining a volume of the reservoir, the reservoir for collecting blood that flows from the vascular access device and into the reservoir via the distal opening, wherein the reservoir comprises a radial divider portion extending at least between the proximal end and the distal end so as to divide the reservoir into at least two chambers; and
a gas permeable membrane disposed within the exterior wall of the body, the membrane allowing gas to exit the reservoir through the membrane while blocking blood from exiting the reservoir thereby allowing the blood sampling device to be used as a vent plug for the vascular access device;
wherein at least a portion of the exterior wall of the body is compressible to reduce the volume of the reservoir thereby forcing blood contained within the reservoir out through the distal opening.

2. The blood sampling device of claim 1, wherein the distal end comprises a male coupler which is inserted into the separate vascular access device.

3. The blood sampling device of claim 2, wherein the male coupler is a male luer.

4. The blood sampling device of claim 2, wherein the male luer includes threads.

5. The blood sampling device of claim 2, wherein the male coupler is not compressible.

6. The blood sampling device of claim 1, wherein the reservoir includes a blood preservative in at least one chamber.

7. The blood sampling device of claim 1, wherein the body includes an indicator of elapsed time since blood sampling.

8. The blood sampling device of claim 1, wherein the entire exterior wall other than the distal end is compressible.

9. The blood sampling device of claim 1, wherein the distal opening includes a wicking material disposed therein.

10. The blood sampling device of claim 1, wherein the distal opening includes a flow restrictor.

11. The blood sampling device of claim 1, wherein the gas permeable membrane is disposed on the proximal end of the exterior wall, a distal surface of the gas permeable membrane being in direct communication with the reservoir, and a proximal surface of the gas permeable membrane being in direct communication with an exterior environment.

12. The blood sampling device of claim 1, wherein the body includes opposing grips for compressing the exterior wall of the body.

13. The blood sampling device of claim 12, wherein the opposing grips are rigid.

14. The blood sampling device of claim 1, wherein the blood sampling device includes a diagnostic component in fluid communication with the reservoir.

15. The blood sampling device of claim 14 wherein [the reservoir comprises at least one chamber, and] the diagnostic component comprises a diagnostic reagent disposed within at least one chamber of the reservoir.

16. A blood sampling device, comprising:
a body shaped and sized for partial insertion into a separate vascular access device, the body comprising an exterior wall having a compressible portion;
a reservoir defined by the exterior wall of the body, the reservoir having an internal volume of at least 0.1 µL, the internal volume defined by an inner surface of the exterior wall, the exterior wall being shaped and sized to receive blood from the separate vascular access device and to eject at least a portion of the blood when the compressible portion is compressed, wherein the reservoir comprises a radial divider portion extending at least between the proximal end and the distal end so as to divide the reservoir into at least two chambers; and
a gas permeable vent disposed within the exterior wall of the body, the gas permeable vent in gaseous communication with the reservoir opening.

17. The blood sampling device of claim 16, wherein the blood is received and ejected through a distal opening in a distal portion of the body.

18. A blood sampling device, comprising:
- a body having an exterior wall forming a male coupler for insertion into a separate vascular access device;
- a reservoir, defined by an inner surface of the exterior wall of the body, the male coupler forming an opening of the reservoir, the reservoir via the opening, wherein the reservoir comprises a radial divider portion extending at least between the proximal end and the distal end so as to divide the reservoir into at least two chambers; and
- a gas permeable vent disposed within the exterior wall of the body, the vent allowing gas to exit the reservoir through the vent while blocking blood from exiting the reservoir;
- wherein at least a portion of exterior wall of the body is compressible to reduce the volume of the reservoir thereby forcing blood contained within the reservoir out the distal opening.

* * * * *